United States Patent [19]

Anderson et al.

[11] Patent Number: 4,994,591
[45] Date of Patent: Feb. 19, 1991

[54] PLATINUM COMPLEXES DERIVED FROM B-SILYAMINES

[75] Inventors: Wayne K. Anderson, Williamsville, N.Y.; Rudiger D. Haugwitz, Bethesda, Md.

[73] Assignee: The Research Foundation of State University of NY, Albany, N.Y.

[21] Appl. No.: 360,363

[22] Filed: Jun. 2, 1989

[51] Int. Cl.$^5$ .............................................. C07F 15/00
[52] U.S. Cl. ..................................... 556/137; 556/9; 556/12; 556/400
[58] Field of Search .................. 556/136, 137, 400, 9, 556/12; 514/287, 184, 6, 63, 79, 492

[56] References Cited

U.S. PATENT DOCUMENTS

| | | | |
|---|---|---|---|
| 4,328,216 | 5/1982 | Toyoshima et al. | 424/184 |
| 4,431,666 | 2/1984 | Bulten et al. | 424/287 |
| 4,500,465 | 2/1985 | Amundsen et al. | 556/137 X |
| 4,550,187 | 10/1985 | Anderson et al. | 556/137 |
| 4,553,502 | 11/1985 | Rochon et al. | 546/8 |
| 4,562,275 | 12/1985 | Speer et al. | 556/7 |
| 4,577,038 | 3/1986 | Totani et al. | 556/137 |
| 4,647,679 | 3/1987 | Panster et al. | 556/9 |
| 4,847,228 | 7/1989 | Saruyama | 556/9 X |
| 4,870,062 | 9/1989 | Kurono et al. | 514/63 |

FOREIGN PATENT DOCUMENTS

288002 10/1988 European Pat. Off. .

OTHER PUBLICATIONS

The Polar Effects of Organosilicon Substituents in Aliphatic Amines, Sommer et al., Synthesis, 1951, vol. 73, pp. 5130–5134.
CA Select Abstract 106:12475d, 1987, Diversity in Antitumor Properties of Selected Silicon Compounds with Various Methyloxyimino Substituents, Fukushima et al.
CA Select Abstract 103:92827W, 1985, Polysilsesquioxanes as neoplasm inhibitors.
CA Select Abstract 102:56149x, 1985.
Unlisted Drugs, Feb. 1984, vol. 36, No. 2, p. 22, Trimethylsilylmethyloxyiminocyclohexane for Treatment of Solid Tumors.
Antitumor Silylalkylated 5–Fluoro Uracils; Pharmaceuticals, p. 4, week 8434, Feb. 1984.
Bioactive Organo–Silicon Compounds, 84–Topics in Current Chemistry, Springer–Verlag, 1979, pp. 113–120.
CA Abstract, vol. 110, No. 9, 1989, p. 683, Organo–Platinum Compounds as Antitumor Agents their Preparation and Formulation.

*Primary Examiner*—Arthur C. Prescott
*Attorney, Agent, or Firm*—Michael L. Dunn; Howard M. Ellis; William J. Crossetta

[57] ABSTRACT

This invention relates to new cis diamino platinum complexes; to compositions comprising these complexes; and to processes for their utility as fungicides, bacteriocides and as inhibitors of the growth of cancer in warm-blooded animals, wherein the complex is of the formula: $[B(CH_2)_nNH_2]_2$ Pt-M and

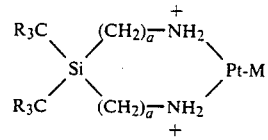

wherein Pt is platinum II or platinum IV; M is selected from $Y_2$, cyclic

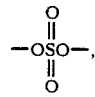

cyclic

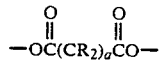

and cyclic

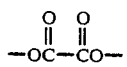

when Pt is platinum II and $X_4$ when Pt is platinum IV; each a is independently 1 or 2; n is from 0–3; each Y is independently —Cl, —Br, —I, —OH, —ONO$_2$, —OSO$_3$ and

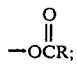

each X is independently selected from Y and two equatorial X's can together further be cyclic

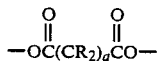

or cyclic

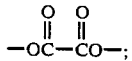

each B is independently selected from aminoalkyl(dialkylsily), aminoalkyl(diphenylsilyl), triphenylsilyl, trialkylsilyl, aminoalkyl(alkyl,phenylsilyl), 2-amino-3,3-dialkyl-3-silacyclo-alkyl, 2-amino-3,3-diphenyl-3-silacycloalkyl, 2-amino-4,4-dialkyl-4-silacycloalkyl, 2-amino-4,4-diphenyl-4-silacycloalkyl and 1-aminoalkyl-1-silacycloalkyl; each R is independently selected from hydrogen and Z substituted and unsubstituted alkyl, alkenyl, cycloalkyl, cycloalkenyl, alkynyl and aryl, provided (Abstract continued on next page.)

that two R's attached to the same or adjacent carbon atoms, or two R's attached through different carbon atoms to the silicon atom, can form Z substituted or unsubstituted alkyl or aryl cyclic ring; and, Z is selected from halogen, carboxylic acid, haloalkyl, alkyl, alkenyl, cycloalkyl, cycloalkenyl, alkynyl and aryl. It is understood that the bond between the platinum and M is 2 or 4.

53 Claims, No Drawings

4,994,591

PLATINUM COMPLEXES DERIVED FROM B-SILYAMINES

This invention was made in part with government support under various contracts awarded by the Department of Health and Human Services, particularly under NCI Contract Numbers CM-27570 and CM-67698-16. The government has certain rights in this invention.

BACKGROUND OF THE INVENTION

There has been a continuing need for new and more effective chemical agents useful in the treatment of cancers in warm blooded animals, especially in human beings. Indeed, the concentrated effort of the National Cancer Institute over the last several years of their increased government funding has identified many new chemical compounds having efficacy in the inhibition of cancers in warm blooded animals, but which, for a multiple of reasons, have not been commercially used in human cancer clinical treatment. Thus, the search for new compounds and pharmaceutical compositions continues.

One object of this invention is to provide new compounds and methods which are useful for inhibiting the growth of cancer.

Another object of this invention is to provide new pharmaceutical compositions which have utility in inhibiting the growth of cancer.

Another object of this invention is to provide compounds having utility as bacteriocides or fungicides.

DESCRIPTION OF THE INVENTION

This invention relates to new cis diamino platinum complexes; to compositions comprising these complexes and to processes for their utility as fungicides, bacteroicides and as inhibitors of the growth of cancer, particularly solid tumor cancer, in warm blooded animals.

In accordance with this invention, new cis diamino platinum compounds are provided of the formula:

$$\begin{array}{c} R_3C \\ \phantom{R_3C}\diagdown \\ \phantom{R_3C}\phantom{\diagdown}Si \\ R_3C\diagup \phantom{\diagdown} \end{array} \begin{array}{c} (CH_2)_{\overline{a}}-NH_2 \\ \phantom{(CH_2)_{\overline{a}}}\diagdown \\ \phantom{(CH_2)_{\overline{a}}}\phantom{\diagdown}Pt-M \\ (CH_2)_{\overline{a}}-NH_2 \end{array}^{+}_{+} =$$

wherein Pt is platinum II or platinum IV; M is selected from $Y_2$, cyclic $$-O\overset{O}{\underset{\underset{O}{\|}}{\overset{\|}{S}}}O-,$$

cyclic $$-O\overset{O}{\overset{\|}{C}}(CR_2)_a\overset{O}{\overset{\|}{C}}O-$$

and cyclic $$-O\overset{O}{\overset{\|}{C}}-\overset{O}{\overset{\|}{C}}O-$$

when Pt is platinum II and $X_4$ when Pt is platinum IV; each a is independently 1 or 2; n is from 0-3; each Y is independently —Cl, —Br, —I, —OH, —ONO$_2$, —OSO$_3$ and $$-O\overset{O}{\overset{\|}{C}}R;$$

each X is independently selected from Y and two equatorial X's can together further be cyclic $$-O\overset{O}{\overset{\|}{C}}(CR_2)_a\overset{O}{\overset{\|}{C}}O-$$

or cyclic $$-O\overset{O}{\overset{\|}{C}}-\overset{O}{\overset{\|}{C}}O-;$$

B is independently selected from aminoalkyl(dialkylsilyl), aminoalkyl(diphenylsilyl), triphenylsilyl, trialkylsilyl, aminoalkyl (alkylphenylsilyl), 2-amino-3,3-dialkyl-3-silacycloalkyl, 2-amino-3,3-dipehnykl-3-silacycloalkyl, 2-amino-4,4-dialkyl-4-silacycloalkyl, 2-amino-4,4-diphenyl-4-silacycloalkyl and 1-aminoalkyl-1-silacycloalkyl; each R is independently selected from hydrogen and Z substituted and unsubstituted alkyl, alkenyl, cycloalkyl, cycloalkenyl, alkynyl and aryl, provided that two R's attached to the same or adjacent carbon atoms, or two R's attached through different carbon atoms to the silicon atom, can form Z substituted or unsubstituted alkyl ro aryl cyclic ring; and, Z is selected from halogen, carboxylic acid, haloalkyl, alkyl, alkenyl, cycloalkyl, cycloalkenyl, alkynyl and aryl. It is understood that the bond between the polatinum and M is 2 or 4.

In a preferred expression of the invention, new cis diamino platinum compounds are provided of the formula:

$$\begin{array}{c} R_3C \\ \phantom{R_3C}\diagdown \\ \phantom{R_3C}\phantom{\diagdown}Si \\ R_3C\diagup \phantom{\diagdown} \end{array} \begin{array}{c} (CH_2)_{\overline{a}}-NH_2 \\ \phantom{(CH_2)_{\overline{a}}}\diagdown \\ \phantom{(CH_2)_{\overline{a}}}\phantom{\diagdown}Pt-M \\ (CH_2)_{\overline{a}}-NH_2 \end{array}^{+}_{+} =$$

wherein Pt is platinum II or platinum IV; M is selected from $Y_2$, cyclic $$-O\overset{O}{\underset{\underset{O}{\|}}{\overset{\|}{S}}}O-,$$

cyclic $$-O\overset{O}{\overset{\|}{C}}(CR_2)_a\overset{O}{\overset{\|}{C}}O-$$

and cyclic

when Pt is platinum II and $X_4$ when Pt is platinum IV; each a is independently 1 or 2; each Y is independently selected from —Cl, —Br, —I, —OH, —ONO$_2$, —OSO$_3$ and

each X is independently selected from —Cl, —Br, —OH and

and two equatorial X's can together further be cyclic

or cyclic

each R is independently selected from hydrogen and Z substituted and unsubstituted alkyl, alkenyl, cycloalkyl, cycloalkenyl alkynyl and aryl, provided that two R's attached to the same or adjacent carbon atoms, or two R's attached through different carbon atoms to the silicon atom, can form Z substituted or unsubstituted alkyl or aryl cyclic ring; and, Z is selected from halogen, carboxylic acid, haloalkyl, alkyl, alkenyl, cycloalkyl, cycloalkenyl, alkynyl and aryl. It is understood that the bond between the platinum and M is 2 or 4.

Further in accord with the invention, new pharmaceutical compositions are provided which contain the compounds of the invention together with a pharmaceutical diluent.

Still further, in addition, a method of the invention is provided where one or more of the afore-described compounds is administered to fungi or bacteria in an amount sufficient to inhibit the growth thereof.

In another method of the invention, one or more of the afore-described compounds is administered to a cancer, particularly solid cancer tumor containing warm blooded animal in an amount sufficient to inhibit the growth of said cancer.

Within the description of the compounds of the invention, particularly the designations R, R' and Z, by the term alkyl, alkenyl and alkynyl is meant alkyl, alkenyl and alkynyl hydrocarbon substituents having from 1 to about 20 carbon atoms and preferably from 1 to about 12 carbon atoms. Such substituents can be straight chained or branched and include isomers thereof. Thus, the term alkyl includes methyl, ethyl, n-propyl, i-propyl, n-butyl, t-butyl, i-butyl, pentyl, hexyl, heptyl and the like up to about 20 carbon atoms. The term alkenyl includes unsaturated hydrocarbons having double bonds therein such as ethene, propene, butene, pentene and the like up to about 20 carbon atoms and preferably from 1 to about 12 carbon atoms. Similarly, the term alkynyl includes unsaturated hydrocarbons having triple bonds up to about 20 carbon atoms and preferably from about 1 to about 12 carbon atoms.

By the term cycloalkyl and cycloalkenyl is meant the alicyclic saturated and unsaturated hydrocarbons containing up to about 20 carbon atoms and preferably from 1 to about 12 carbon atoms, such as cyclopropyl, methylcyclopropyl, cyclobutyl, ethylcyclobutyl, cyclopentyl, cyclohexyl, ethenylcyclobutyl, cyclohexene, cyclohexediene and the like.

By the term aryl, is meant cyclic aromatic and heteroaromatic structures which include benzene, naphthalene, pyridine, pyrimidine, quinoline, thiophene, indole, phenanthrene, anthracene, etc., up to a total of about 20 carbon atoms. The preferred aryl substituents are phenyl and napthyl.

When referring to haloalkyl is meant any alkyl group up to about 20 carbon atoms and preferably from 1 to about 12 carbon atoms, as previously described containing one or more halogen atoms, preferably selected from chlorine, bromine and fluorine.

By the term carboxylic acid is meant an acid of the general structure:

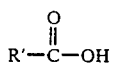

wherein R' is selected from hydrogen and Z substituted or unsubstituted alkyl, alkenyl, alkynyl, cycloalkyl and aryl as previously described. Such acids particularly include formic, acetic, propionic, butyric, valeric and the like carboxylic acids up to about 20 carbon atoms.

Typically, the preparation of the compounds of the invention can be attained through several routes. The requisite silylamine ligands where B is trialkylsilane or triphenylsilane can be prepared by subjecting the appropriate haloalkyl silanes to a Gabriel reaction to obtain, upon hydrazinolysis, the desired amine. This sequence is known in the art and is described in such publications as Sommer et al. J. Am. Chem. Soc. 73, 5130, (1951). Conversion of haloalkyl silanes to the azide and subsequent lithium aluminum hydride reduction to the amine is another route.

High yields, in the preparation of the preferred compounds of the invention, have been generally attained by reaction of a chlorinated silane with sodium azide; reducing the bis(azido) silane product to an amine; substituting the amine with a halogenated platinum; and, substituting the halogen of the platinum with an appropriate M substituent, in accordance with the following schematic:

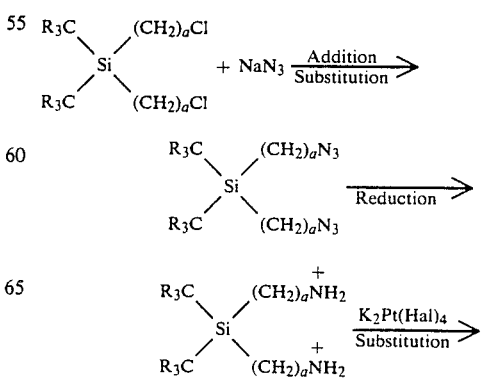

-continued

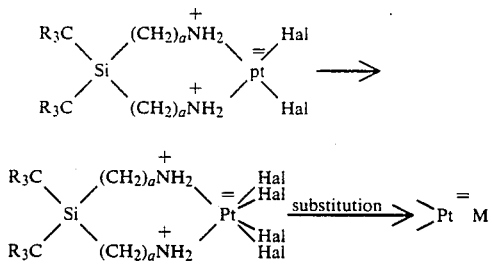

The silane reactants containing the R substituents of the invention are generally readily available. L. Sommer and J. Rockett in a paper received Apr. 11, 1951, at the State College, Penna., describe the polar effects of various organosilicon substituents in aliphatic amines and methods for preparing such amines useful as reactants for this invention. Synthesis, 1102 (1982) and J.O.C., 32, 511 (1967) describe the preparation of other organosilanes useful in this invention.

The halogenated silane reactants readily react with sodium azide, generally in the presence of a polar solvent, such as 1,3-dimethyl-3,4,5,6-tetrahydro-2(1H)-pyrimidinone (DMPU), sulfolane, and the like, at elevated temperatures, to form the bis(azido) silane. The bis azide silane is typically removed from the solvent by distillation. Careful control of distillation when using DMPU is essential as low temperature distillation can result in the bis azide being contaminated with significant quantities of DMPU while high temperature distillation can result in a severe explosion. The use of sulfolane as the solvent has provided high yields of noncontaminated product with a reduced threat of explosion.

The bis(azido) silane product can be easily reduced, typically by contact with lithium aluminum hydride in an appropriate solvent such as ether at low temperature (0° C.). Complexation of the resulting amine with an appropriate platinum compound such as potassium tetrachloroplatinate in water-methanol or in helium degassed water under an argon atmosphere results in the formation of the bis silane amino dichloro platinum complex. Further reaction of the complex, with chlorine gas at elevated temperatures, forms the platinum IV complex. Reduction to the platinum IV complex can also be achieved by other means such as with hydrogen peroxide.

Once the bis silane amino halogenated platinum II or IV complex is formed, attaining of the appropriate M substituent can be easily achieved by simple substitution reaction with an appropriate leaving group including dicarboxylic acids, such as for example 1,1-cyclobutanedicarboxylic acid, methylaminodiacetic acid and oxalic acid.

The compounds of the invention can be converted to their acid or base salt for convenience. Generally a strong mineral acid such as HCl, $H_2SO_4$ and the like is convenient in the manufacture of the acid salt, but generally any acid such as acetic acid, the sulfonic acids and many of the carboxylic acids will readily form an acid salt with the base structure compounds of the invention. Base salts can be generally attained by reacting the compounds of the described general structure with an appropriate base such as sodium hydroxide, ammonia, substituted amine or the like. One preferred basic salt is the sodium salt of a carboxyphthalato group.

The method in accordance with the present invention for inhibiting the growth of microorganisms and especially bacterial organisms comprises contacting the organism for a sufficient time with a sufficient concentration of the compounds, or compositions thereof, of the invention, suitable compounds being those previously generically and specifically described. In general the sufficient concentration of the compound is from about 0.01 to about 10 micrograms per milliliter of medium containing the organism. For very difficult microorganisms, e.g. fusobacteria, the concentration required may be substantially higher, e.g. as much as 50 micrograms or more per milliliter.

The medium on or within which the compounds of the invention can be used may be any solid or liquid. Examples of medium upon which the compounds may be used are organic tissue, surfaces, floors, walls, hardware, implements in general, paints, textiles, leather, synthetic resins, foods, medicines, and other like substances. The compounds may be used in or on the medium as antiseptics, disinfectants, antimicrobial medicines or preservatives. They also may be used as additives to soaps, deodorants, and sterilizing solutions to enhance or provide antimicrobial properties to such products. A compound of the invention may be used alone, in mixture with other compounds of the invention, in mixture with other inhibiting compounds, with diluents, extenders, and carriers or the like. It is to be understood that the above sufficient concentrations are those required to be in actual contact with the microorganism and substantially higher concentrations may be required in preparations where penetration through a substance is required in order to contact the microorganism with the compounds of the invention. The sufficient time is the time required to inhibit the growth of the microorganism and may depend upon the extent of inhibition required. Generally, the microorganism is inhibited by the compounds in from about 10 seconds to 30 minutes.

Microorganism as used herein includes any microorganism whose growth can be inhibited by the compositions of the invention. Such microorganisms include almost all bacteria and also include many fungi. It is also possible that some other protists and perhaps even some viruses are included.

As previously discussed, another method of the invention comprises the chemical inhibition of the growth of cancerous tumor cells. In accordance with this method, an organism containing tumor cells is administered an effective tumor inhibiting concentration of a pharmaceutical composition comprising at least one compound of the invention preferably in acid salt form.

The quantity of the compound sufficient for treatment of cancer tumors varies depending upon the size of the warm blooded animal involved, upon the type of solid tumor and upon the species of the animal involved. In general, for most applications the effective tumor inhibiting concentration of the compound of the invention usually ranges between about 0.5 and 1500 milligrams per kilogram of body weight of the organism being treated. The preferred concentration is between about 1 and about 300 milligrams per kilogram of body weight of the organism being treated. In general, large animals require less of any pharmaceutical compound per kilogram of body weight than smaller animals.

The method of the invention has numerous advantages over prior treatment methods which will become clear from the specification as set forth below. Many compounds of the invention have a broad range of activity against multiple tumors over a broad range of doses, including activity against cisplatinum resistant L1210 tumors. This makes the drug much more suitable for widespread use against different types of tumors and lowers the risk of toxic dose.

As used herein the term leukemic cancer refers to all cancers or neoplasms of the hemopoietic and immune systems (blood and lymphatic system). The term solid tumor as used herein are those epithelial neoplasms, such as skin and stomach cancer; connective tissue neoplasms, such as bone and smooth muscle cancer; neoplasms of the nervous system; neoplasms of multiple tissues, such as breast cancer and kidney cancer; and miscellaneous neoplasms such as placenta cancer and ovary cancer Of particular interest is the activity of various compounds herein on the solid cancer tumors of the colon, lung, and breast.

The solid tumors are believed more difficult to treat than leukemic cancers as they are slower growing and dense. It is believed that most treatment materials are effective at the time of cell division. The slower growth means fewer cell divisions cell. The dense mass of tumor does not allow as ready access of the treatment compound to the tumor as the more widely separated cells of the leukemic blood cancers. Therefore, the activity of the compounds of the invention against solid tumors is unusual and of interest for solid tumor treatment.

Any suitable dosage may be given in the method of the invention. The type of and the amount of dosage will vary widely depending on the species of the warm blooded animal, body weight, and tumor being treated. Generally, a dosage of between about 2 milligrams per kilogram of body weight and about 400 milligrams per kilogram of body weight is suitable. Generally, the dosage per kilogram in man is lower than for small warm blooded mammals.

The pharmaceutical compositions of the invention may comprise a single compound of the invention or mixtures thereof with other compounds of the invention or other cancer inhibiting compounds. Pharmaceutical compositions can be in the form of a dosage unit and can also comprise diluents, extenders, carriers, and the like. The unit may be in solid or gel form such as pills, tablets, capsules, and the like or in liquid form suitable for oral, rectal, topical, or parenteral administration.

The method of treatment may be any suitable method which is effective in treatment of the particular tumor which is under treatment. Treatment may be oral, rectal, topical, parenteral, and the like. The method of applying an effective amount also varies depending on the tumor being treated. It is believed that parenteral treatment by intravenous, subcutaneous, or intramuscular application, formulated with an appropriate carrier, additional cancer inhibiting compound(s) or diluent to facilitate application, will be the preferred method of administering the compounds of the invention in warm blooded animals.

The following examples are meant to illustrate the invention and are not to be viewed as a limitation thereof. All temperatures are in degrees, centigrade unless otherwise denoted.

EXAMPLE I

Trimethylsilylmethylazide

Chloromethyltrimethylsilane (12.26 g; 0.1 mol) was added to a stirred suspension of finely powdered sodium azide (7.16 g; 0.11 mol) in 1,3-dimethyl-3,4,5,6-tetrahydro-2(1H)-pyrimidinone (DMPU, 50 mL). The mixture was stirred at 80° C. for 14 hours. The cloudy reaction mixture was allowed to cool to room temperature and the reaction mixture was carefully distilled to give trimethylsilylmethylazide as a colorless liquid (10.28 g; 80% yield).

EXAMPLE II

Trimethylsilylmethylamine

A suspension of lithium aluminum hydride (3.04 g; 0.08 mol) in anhydrous ether (120 mL) was stirred at 0° C. for 30 minutes under argon. A solution of trimethylsilylmethylazide (10.32 g; 0.08 mol) in anhydrous ether (40 mL) was added dropwise to the stirred lithium aluminum hydride suspension over a period of 45 minutes while the temperature was maintained at 0° C. The cooling bath was removed when the addition was completed and the stirred reaction mixture was allowed to warm to room temperature over a period of 2 hours. The reaction mixture was carefully quenched with water (3.5 mL) followed by 10% aqueous sodium hydroxide (4.0 mL). The mixture was filtered and the solid was washed repeatedly with ether. The combined ether solution was dried (sodium sulfate) and the ether was removed in vacuo (0°–5° C.). The crude residue was allowed to stand at room temperature over potassium hydroxide pellets for 1 hour with intermittent shaking and then, without removal of the potassium hydroxide, the product was distilled in an argon atmosphere giving 5.06 g (60% yield) of aminomethyltrimethylsilane that was stored under an argon atmosphere.

EXAMPLE III

Bis-(azidomethyl)dimethylsilane

Bis-(chloromethyl)dimethylsilane (15.7 g; 0.1 mol) was added in one portion to a stirred suspension of sodium azide (13.0 g; 0.2 mol) in tetramethylenesulfone (sulfolane; 50 mL) at 40° C. Solid sodium carbonate (4–5 granules) was added and the mixture was heated at 55°–60° C. for 16 hours under a nitrogen atmosphere. The turbid white reaction mixture was cooled to room temperature and the product was distilled directly from the mixture to give 14.96 g (88% yield) of the titled compound having a boiling point of 22°–23° C./37 mm.

EXAMPLE IV

Bis-(aminomethyl)dimethylsilane

A solution of bis-(azidomethyl)diethylsilane (14.96 g; 0.088 mol) in anhydrous ether (50 mL) was added dropwise over a 45 minute period to a suspension of lithium aluminum hydride (6.69 g, 0.176 mol) in anhydrous ether (200 mL) at 0° C. under nitrogen. The mixture was then stirred at 0° C. for 30 minutes and at 20° C. for 30 minutes. The mixture was cooled to 0° C. and water (8 mL) was added carefully. A 10% sodium hydroxide solution (7 mL) was added, the mixture was filtered and the lithium salts were washed repeatedly with ether. The combined ether solution was dried (sodium sulfate) and the ether was removed in vacuo at 0° C. Potassium hydroxide pellets were added to the colorless liquid residue, the mixture was allowed to stand overnight and was distilled to give 4.3 g (42% yield) of the titled compound, as a colorless liquid.

EXAMPLE V

Cis-[bis-Trimethylsilylmcthylamino)]dichloroplatinum-(II)

A solution of trimethylsilylmethylamine (2.09 g; 0.02 mol) in methanol (8 mL) and water (4 mL) was added to a filtered solution of potassium tetrachloroplatinate (4.185 g; 0.01 mol) in helium degassed water (28 mL) that was stirred in the dark under an argon atmosphere. The mixture was stirred under these conditions for 18 hours at 18°-20° C. The precipitated product was collected and washed sequentially with cold water, cold 1N HCl, cold (0° C.) ethanol and ether. The grayish-white solid was dried in vacuo to give 2.78 g (58%) of the titled compound.

EXAMPLE VI

Cis-[bis-(Trimethylsilylmethyamino)]tetrachloroplatinum(IV)

Chlorine gas was slowly bubbled (ca. 2–3 bubbles per second) through a stirred suspension of bis-(trimethylsilylmethylamino)dichloroplatinum(II) 0.5 g; 1.059 mmol) in 0.5 N HCl (10 mL) maintained at 60° C. The solid immediately became yellow in color. The chlorine gas was bubbled into the suspension (55°-60° C.) for 2 hours. The mixture was cooled to room temperature and excess chlorine was removed by bubbling air rapidly through the reaction mixture for 2 hours. The mixture was concentrated to dryness in vacuo and the solid yellow residue was dissolved in methanol. The methanol solution was filtered and concentrated to dryness in vacuo to yield a yellow solid that was crystallized from acetone-water (1:3) to yield 0.496 g (82%) of the titled compound.

EXAMPLE VII

Cis-[bis(aminomethyl)dimethylsilane]dichloroplatinum-(II)

A solution of bis-(aminomethyl)dimethylsilane (1.0 g, 8.62 mmol) in argon degassed methanol (9 mL) was added rapidly to a stirred solution of potassium tetrachloroplatinate (3.58 g; 8.62 mmol) in argon degassed water (36 mL) that was maintained under an argon atmosphere. The mixture was stirred at 20° C., protected from light, for 16 hours. The solid was collected on a sintered glass funnel, washed with water, 1N HCl, cold ethanol and ether and then dried to give 2.5 g (75% yield) of the titled compound as an off-white solid.

EXAMPLE VIII

Cis-[bis(aminomethyl)dimethylsilane]tetrachloroplatinum(IV)

The oxidation of cis-[bis(aminomethyl)dimethylsilane] dichloroplatinum(II) (1.0 g; 2.62 mmol) was conducted as described for the synthesis of Example VI. The bright yellow solid that was obtained when the mixture was concentrated to dryness in vacuo was dissolved in acetonitrile-water (3:2), the solution was filtered and concentrated in vacuo until only a small amount of solvent remained. The mixture was filtered. The solid was washed with methanol then with ether and dried to give 0.932 g (79% yield) of the titled compound as a yellow solid.

EXAMPLE IX

Cis-[bis(aminomethyl)dimethylsilyl]diiodoplatinum(II)

Solid anhydrous potassium iodide (6.644 g) was added to a solution of 4.15 g of potassium tetrachloroplatinate in 60 ml of argon degassed water. The mixture was stirred, in the dark under argon, for 15 minutes before a solution, containing 1.16 g of bis(aminomethyl)dimethylsilane in 2 ml of argon degassed water, was added all at once to the mixture. Immediately, a yellow solid began to precipitate. The mixture was stirred at 16° C. for 70 minutes. The solid was then filtered and washed with 1 ml portions of water until the washings were colorless. The resulting product was then washed in cold ethanol (5 ml), thereafter in anhydrous ether and air dried. The resulting yellow electrostatic solid was recovered and found to comprise 4.35 g (77% yield) of the titled compound.

EXAMPLE X

Cis-[bis(aminomethyl)dimethylsilyl]platinum(II) sulfate

Cis-[bis-(aminomethyl)dimethylsilyl]diiodoplatinum-(II) from Example IX (4.536 g) was added to a solution containing slightly less than the stoichiometric amount of silver sulfate (2.49 g) in 400 ml of distilled water. The mixture was stirred for four hours in the dark. The stirred mixture was then filtered through a sintered glass funnel and then through a 0.45 micron nylon filter membrane. The resulting clear solution was concentrated to 200ml and comprised the titled compound.

EXAMPLE XI bis(aminomethyl)dimethylsilylcyclobutane-1,1-dicarboxato(2-)0,0'1platinum.

1,1-Cyclobutanedicarboxylic acid (1.184 g) was added to a solution of barium hydroxide octahydrate (2.524 g) in 120 ml of water and stirred for 10 minutes. The resulting aqueous solution of barium 1,1-cyclobutane dicarboxylate was then added to 8.0 moles of the aqueous sulfate solution prepared in Example X. This reaction mixture was stirred for one hour at 20 degrees centigrade and the resulting suspension was filtered through a 0.45 micron nylon filter.

The clear filtrate from the above was concentrated to dryness to give a white crystalline residue, which, after being washed with ethanol and thereafter with anhydrous ether, was analyzed as comprising 3.61 grams of the titled product as a white crystalline solid.

EXAMPLE XII

L-1210 Leukemia activity, in vivo

Various of the compounds of the invention, prepared in accord with Examples I-XI, were tested for antitumor activity in-vivo using standard L-1210 and standard L-1210/DDPt leukemia test procedures, in mice, with the compound 5-Fluorouracil (5-FU) and cis-diamino-dichloroplatinum (cis-DDPt) representing controls. The L-1210/DDPt test procedure comprises the treatment of mice, bearing the L-1210 tumor, that were specifically raised to be resistant to DDPt treatment. The compounds produced by the process of Examples VII and VIII were tested to shown efficacy The designations a,b, and c merely refer to differer samples prepared in accord with the examples.

The test system was that employed by the Nation Cancer Institute (NCI) for the screening of anti-tum agents, according to the protocols set out at Cancer Chemo. Reports 3(2) pages 1–103, (1972). The L-1210/DDpt test comprises the same methodology as the L-1210 test, however, uses cis-DDPt resistant L-1210 tumor cell bearing mice. In the study ascitic fluid containing approximately $1.0 \times 10^5$ cells was implanted into the peritoneal cavity of CDFl mice on day 0. The compounds of the invention were administered, in saline, intraperitoneally in single injections at 4–5 different dose levels, using 6 or 10 mice per dose level, beginning on day 1 and thereafter on the days indicated in the table under Dose Day. Treated control animals received cis-DDPt (10 mice/dose level) or 5-FU (1 dose level). Untreated control animal survival was within the range specified by the afore-cited protocols. The test was run for 30 days or until the animal died, whichever occurred first. Test criteria was in accord with NCI protocol. Thirty Day Survivals (TDS), were evaluated on day 30 of the test and sets out the number of survivors/number of animals tested. Body Weight Difference (BWD) was evaluated in accord with protocol and comprises the average body weight change of the test group minus that of untreated control animals. %T/C data was calculated through mean survival time of the test animals compared to the untreated control animals expressed as a percentage. Therefore %T/C represents the mean survival time of compound treated animals divided by the mean survival time of untreated control animals Median %ILS is determined by %T/C −100 and represents the percent increase in life-span of the test animal. Tumor burden (BDN) represents the approximate $\log_{10}$ change in viable tumor cell population at the end of treatment compared to the start of treatment. A −6 Log change represents 99.9% reduction and +3 Log change represents a 1,000 fold increase in viable tumors Table I comprises the results of the L-1210 test protocol, while Table II comprises the L-1210/DDPt test protocol.

TABLE I

L-1210 LEUKEMIA IN VIVO

| Compd | Dose (mg/kg) | Dose Days | TDS | BWD (grams) | % T/C | Median % ILS | Tumor BDN |
|---|---|---|---|---|---|---|---|
| Example VIIa | 80 | 1,5,9 | 0/6 | −4.1 | 137 | | |
| | 40 | 1,5,9 | 4/6 | −1.5 | 348 | | |
| | 20 | 1,5,9 | 3/6 | 0.0 | 348 | | |
| | 10 | 1,5,9 | 3/6 | −1.5 | 348 | | |
| Example VIIb | 80 | 1,5,9 | 0/10 | −5.2 | — | | |
| | 40 | 1,5,9 | 0/10 | −3.8 | 131 | | |
| | 20 | 1,5,9 | 5/10 | −1.1 | 337 | | |
| | 10 | 1,5,9 | 3/10 | −1.1 | 235 | | |
| | 5 | 1,5,9 | 1/10 | −0.1 | 280 | | |
| Example VIIIa | 80 | 1,5,9 | 0/6 | −5.6 | 96 | | |
| | 40 | 1,5,9 | 4/6 | −3.0 | 348 | | |
| | 20 | 1,5,9 | 4/6 | −1.8 | 348 | | |
| | 10 | 1,5,9 | 3/6 | −0.6 | 348 | | |
| Example VIIIb | 80 | 1,5,9 | 0/10 | −4.3 | 112 | | |
| | 40 | 1,5,9 | 4/10 | −2.2 | 258 | | |
| | 20 | 1,5,9 | 1/10 | −1.5 | 216 | | |
| | 10 | 1,5,9 | 0/10 | −0.8 | 168 | | |
| | 5 | 1,5,9 | 0/10 | −0.1 | 157 | | |
| Example VIIc | 30 | 1,5,9 | 5/6 | | | +141 | −6.6 |
| | 20 | 1,5,9 | 2/6 | | | +88 | −5.8 |
| | 15 | 1,5,9 | 6/10 | | | +83 | −6.2 |
| | 10 | 1,5,9 | 3/10 | | | +152 | −5.8 |
| | 5 | 1,5,9 | 3/10 | | | +141 | −5.8 |
| 5-FU | 20 | 1-5 | 0/10 | | | +61 | −1.3 |
| Cis-DDPt | 20 | 1,5,9 | 0/10 | | | +43 | +2.4 |
| | 10 | 1,5,9 | 3/10 | | | +94 | −5.8 |
| | 5 | 1,5,9 | 0/10 | | | +80 | +0.7 |
| | 2.5 | 1,5,9 | 0/10 | | | +28 | +2.7 |

TABLE II

L-1210 DDPt LEUKEMIA IN VIVO

| Compd | Dose (mg/kg) | Dose Days | TDS | Median % ILS | Tumor BDN |
|---|---|---|---|---|---|
| Example VIIc | 30 | 1,5,9 | 5/6 | +60 | +1.7 |
| | 20 | 1,5,9 | 2/6 | +50 | −5.7 |
| | 15 | 1,5,9 | 6/10 | +98 | −6.0 |
| | 10 | 1,5,9 | 3/10 | +14 | −6.7 |
| | 5 | 1,5,9 | 3/10 | +35 | −5.4 |
| 5-FU | 20 | 1-5 | 0/10 | +98 | −3.7 |
| Cis-DDPt | 20 | 1,5,9 | 0/10 | +5 | +3.1 |
| | 10 | 1,5,9 | 3/10 | +8 | +3.1 |
| | 5 | 1,5,9 | 0/10 | +4 | +3.2 |
| | 2.5 | 1,5,9 | 0/10 | +4 | +3.2 |

We claim:

1. A cis diamino platinum compound of the formula:

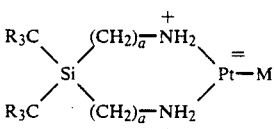

wherein Pt is platinum II or platinum IV; M is selected from $Y_2$, cyclic

cyclic

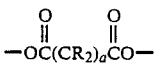

and cyclic

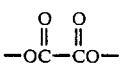

when Pt is platinum II and $X_4$ when Pt is platinum IV; each a is independently 1 or 2; each Y is independently selected from —Cl, —Br, —I, —OH, —ONO$_2$, —OSO$_3$ and

each X is independently selected from —Cl, —Br, —OH

and two equatorial X's can together further be cyclic

or cyclic

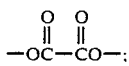

each R is independently selected from hydrogen and Z-substituted and unsubstituted alkyl, alkenyl, cycloalkyl, cycloalkenyl, alkynyl and aryl, provided that two R's attached to the same or adjacent carbon atoms, or two R's attached through different carbon atoms to the silicon atom, can form Z substituted or unsubstituted alkyl or aryl cyclic ring; and, Z is selected from halogen, carboxylic acid, haloalkyl, alkyl, alkenyl, cycloalkyl, cycloalkenyl, alkynyl and aryl.

2. A compound of claim 1 wherein each a is 1.
3. A compound of claim 1 wherein each a is 2.
4. A compound of claim wherein each R is selected from unsubstituted alkyl and hydrogen.
5. A compound of claim 1 wherein Pt is platinum II.
6. A compound of claim 1 wherein Pt is platinum IV.
7. A compound of claim 5 wherein M is selected from cyclic

cyclic

and cyclic

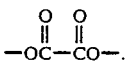

8. A compound of claim 6 wherein X is selected from cyclic

and cyclic

9. A compound of claim 5 wherein M is selected from —Cl, —Br, —I, —OH, —ONO$_2$, —OSO$_3$ and

10. A compound of claim 6 wherein X is selected from —Cl, —Br, —OH and

11. An acid salt of a compound of claim 1.
12. The hydrochloric acid salt of a compound of claim 1.

13. A base salt of a compound of claim 1.
14. A Cis-[bis(aminomethyl)dimethylsilane]dichloroplatinum(II) compound of claim 1.
15. An acid salt of the compound of claim 14.
16. A base salt of the compound of claim 14.
17. A Cis-[bis(aminomethyl)dimethylsilane]tetrachloroplatinum(IV) compound of claim 1.
18. An acid salt of the compound of claim 17.
19. A base salt of the compound of claim 17.
20. The sodium base of a carboxy phthalato group salt of a compound of claim 1.
21. A pharmaceutical composition comprising a pharmaceutical diluent and at least one cis diamino platinum compound of the formula:

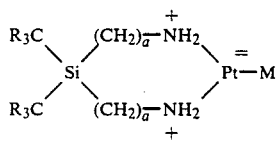

wherein Pt is platinum II or platinum IV; M is selected from Y$_2$, cyclic

cyclic

and cyclic

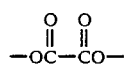

when Pt is platinum II and X$_4$ when Pt is platinum IV; each a is independently 1 or 2; each Y is independently selected from —Cl, —Br, —I, —OH, —ONO$_2$, —OSO$_3$ and

each X is independently selected from —Cl, —Br, —OH and

and two equatorial X's can together further be cyclic

or cyclic

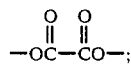

each R is independently selected from hydrogen and Z substituted and unsubstituted alkyl, alkenyl, cycloalkyl, cycloalkenyl, alkynyl and aryl, provided that two R's attached to the same or adjacent carbon atoms, or two R's attached through different carbon atoms to the silicon atom, can form Z substituted or unsubstituted alkyl or aryl cyclic ring; and, Z is selected from halogen, carboxylic acid, haloalkyl, alkyl, alkenyl, cycloalkyl, cycloalkenyl, alkynyl and aryl.

22. The pharmaceutical composition of claim 21 comprising an acid salt of at least one of said platinum compounds.

23. The pharmaceutical composition of claim 21 comprising a base salt of at least one of said platinum compounds.

24. A pharmaceutical composition of claim 21 wherein each a is 1.

25. A pharmaceutical composition of claim 21 wherein each a is 2.

26. A pharmaceutical composition of claim 21 wherein each R is selected from unsubstituted alkyl and hydrogen.

27. A pharmaceutical composition of claim 21 wherein Pt is platinum II.

28. A pharmaceutical composition of claim 21 wherein Pt is platinum IV.

29. A pharmaceutical composition of claim 27 wherein M is selected from cyclic

cyclic

and cyclic

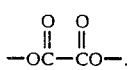

30. A pharmaceutical composition of claim 28 wherein X is selected from cyclic

and cyclic

31. A pharmaceutical composition of claim 27 wherein M is selected from —Cl, —Br, —I, —OH, —ONO$_2$, —OSO$_3$ and

32. A pharmaceutical composition of claim 28 wherein X is selected from —Cl, —Br, —OH and

33. A pharmaceutical composition of claim 21 comprising at least one compound selected from the group consisting of Cis-tetrachloroplatinum(IV) and Cis-dichloroplatinum(II).

34. A pharmaceutical composition of claim 21 comprising at least one acid salt of a compound selected from the group consisting of Cis-tetrachloroplatinum(IV) and Cis-dichloroplatinum(II).

35. A pharmaceutical composition of claim 21 comprising at least one base salt of a compound selected from the group consisting of Cis-tetrachloroplatinum(IV) and Cis-dichloroplatinum(II).

36. A method for inhibiting the growth, in a warm blooded animal, of a cancer tumor comprising administering to said warm blooded animal, an effective a cancer tumor inhibiting amount of a cis diamino platinum compound of the formula:

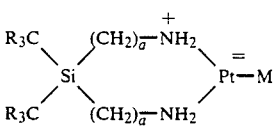

wherein Pt is platinum II or platinum IV; M is selected from Y$_2$, cyclic

cyclic

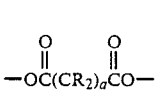

and cyclic

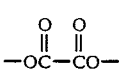

when Pt is platinum II and X$_4$ when Pt is platinum IV; each a is independently 1 or 2; each Y is independently selected from —Cl, —Br, —I, —OH, —ONO$_2$, —OSO$_3$ and

each X is independently selected from —Cl, —Br, —OH and

and two equatorial X's can together further be cyclic

or cyclic

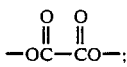

each R is independently selected from hydrogen and Z substituted and unsubstituted alkyl, alkenyl, cycloalkyl, cycloalkenyl, alkynyl and aryl, provided that two R's attached to the same or adjacent carbon atoms, or two R's attached through different carbon atoms to the silicon atom, can form Z substituted or unsubstituted alkyl or aryl cyclic ring; and, Z is selected from halogen, carboxylic acid, haloalkyl, alkyl, alkenyl, cycloalkyl, cycloalkenyl, alkynyl and aryl.

37. The method of claim 36 wherein said compound comprises an acid or base salt of said platinum compound.

38. The method of claim 36 wherein the quantity of said compound administered is between about 0.5 and about 1,500 milligrams per kilogram of body weight of the warm blooded animal.

39. The method of claim 38 wherein said quantity is between about 1 and about 300 milligrams per kilogram of body weight of the warm blooded animal.

40. The method of claim 36 wherein said cancer tumor is a leukemia.

41. The method of claim 36 wherein said cancer tumor is a solid cancer tumor.

42. The method of claim 41 wherein said cancer tumor is selected from solid tumor of the colon, breast and lung.

43. The method of claim 40 wherein said cancer tumor is melanotic melanoma.

44. A pharmaceutical preparation adapted for administration to a warm blooded animal to inhibit the growth of a cancer tumor, in vivo, comprising, per dosage unit, a cancer tumor inhibiting effective non-toxic amount of a compound of claim 1.

45. A pharmaceutical preparation adapted for administration to a warm blooded animal to inhibit the growth of a cancer tumor, in vivo. comprising, per dosage unit, a cancer tumor inhibiting effective non-toxic amount of a compound of claim 11.

46. A pharmaceutical preparation adapted for administration to a warm blooded animal to inhibit the growth of a cancer tumor, in vivo. comprising, per dosage unit, a cancer tumor inhibiting effective non-toxic amount of a compound of claim 13.

47. A pharmaceutical preparation adapted for administration to a warm blooded animal to inhibit the growth of a cancer tumor, in vivo. comprising, per dosage unit, a cancer tumor inhibiting effective non-toxic amount of a compound comprising at least one of Cis-tetrachloroplatinum(IV) and Cis-dichloroplatinum(II).

48. A pharmaceutical preparation adapted for administration to a warm blooded animal to inhibit the growth of a cancer tumor, in vivo. comprising, per dosage unit, a cancer tumor inhibiting effective non-toxic amount of a compound comprising at least one base or acid salt of a compound selected from Cis-tetrachloroplatinum(IV) and Cisdichloroplatinum(II).

49. A compound of the formula:

$$[B(CH_2)_n NH_2]_2 Pt\text{-}M$$

wherein Pt is platinum II or platinum IV; M is selected from $Y_2$, cyclic

cyclic

and cyclic

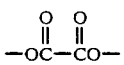

when Pt is platinum II and $X_4$ when Pt is platinum IV; n is from 0–3; each Y is independently selected from the group consisting of —Cl, —Br, —I, —OH, —ONO$_2$, —OSO$_3$ and

each X is independently selected from Y and two equatorial X's can together further be cyclic

or cyclic

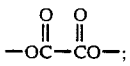

and, each B is independently selected from aminoalkyl(dialkylsilyl), aminoalkyl(diphenylsilyl), triphenylsilyl, trialkylsilyl, aminoalkyl(alkylphenylsidyl), 2-amino-3,3-dialkyl-3-silacycloalkyl, 2-amino-3,3-diphenyl-3-silacycloalkyl 2-amino-4,4-dialkyl-4-silacycloalkyl, 2-amino-4,4-diphenyl-4-silacycloalkyl and 1-aminoalkyl-1-silacycloalkyl.

50. A pharmaceutical composition comprising at least one compound of claim 49.

51. A pharmaceutical composition comprising an acid salt of at least one compound of claim 49.

52. A pharmaceutical composition comprising a base salt of at least one compound of claim 49.

53. An acid or base salt of a compound of claim 49.

* * * * *

UNITED STATES PATENT AND TRADEMARK OFFICE
CERTIFICATE OF CORRECTION

PATENT NO.  : 4,994,591

DATED       : February 19, 1991

INVENTOR(S) : Wayne K. Anderson et al.

It is certified that error appears in the above-identified patent and that said Letters Patent is hereby corrected as shown below:

In Claims 33, 34, 35 and 47 "Cis-tetrachloroplatinum(IV) and Cis-dichloroplatinum(II)" should read --Cis-[bis(aminomethyl)dimethylsilane] tetrachloroplatinum(IV) and Cis-[bis(aminomethyl)dimethylsilane]dichloroplatinum(II)--

Signed and Sealed this

Fourteenth Day of July, 1992

*Attest:*

DOUGLAS B. COMER

*Attesting Officer*     *Acting Commissioner of Patents and Trademarks*